United States Patent

Kleiner et al.

Patent Number: 5,811,575
Date of Patent: Sep. 22, 1998

[54] PROCESS FOR PREPARING VINYL-PHOSPHONIC ACIDS

[75] Inventors: Hans-Jerg Kleiner, Kronberg; Günter Roscher, Kelkheim, both of Germany

[73] Assignee: Clariant GmbH, Frankfurt, Germany

[21] Appl. No.: 857,318

[22] Filed: May 16, 1997

Related U.S. Application Data

[63] Continuation of Ser. No. 435,829, May 5, 1995, abandoned.

[30] Foreign Application Priority Data

May 6, 1994 [DE] Germany ............... 44 16 018.6

[51] Int. Cl.$^6$ .................................................. C07F 9/38
[52] U.S. Cl. ................................. 562/8; 562/20
[58] Field of Search ........................... 562/8, 20

[56] References Cited

U.S. PATENT DOCUMENTS

| | | | |
|---|---|---|---|
| 4,388,252 | 6/1983 | Dürsch et al. ................... | 260/968 |
| 4,426,336 | 1/1984 | Kleiner et al. ................... | 260/986 |
| 4,486,357 | 12/1984 | Krause et al. ................... | 260/502.4 R |
| 5,132,444 | 7/1992 | Nothemann et al. ............. | 558/83 |

FOREIGN PATENT DOCUMENTS

| | | |
|---|---|---|
| 0 068 350 | 6/1981 | European Pat. Off. . |
| 0 032 663 | 7/1981 | European Pat. Off. . |
| 0 038 466 | 10/1981 | European Pat. Off. . |
| 0 047 461 | 3/1982 | European Pat. Off. . |
| 0 456 049 | 11/1991 | European Pat. Off. . |

OTHER PUBLICATIONS

CA:120: 134678 Mechanism of Phosphorylation Reaction of 2 Haloalkylphosphonic Acids., Segall Phos, Sulf. Silicon. Rel. 75(1–4) 191–4 1993.
CA 69 19307—Prep of Vinyl Phosphic Acid Anhydride. Abst SU 193508 1967, Mar., 13.
CA 117:69933 Synthesis P31 & C13 NMR Studies of Pyrophosphonic Acids Ohms, Phos Sulf. Silic Relat El 68(1–4) 77–89 1992.
CA 96:52500 Vinyl Phosphonic Acid Der. Kleiner Abst. DE 3014737 Oct. 22, 1981.
CA 95:187421 Vinyl Phosphonic Acid Derivatives Duerseh Abst of DE 3001894—1981.
Morrison & Boyd, "Organic Chemistry," Allyn and Bacon, Inc., Boston (1973), p. 157.
Lowry & Richardson, "Mechanism and Theory in Organic Chemistry," Harper & Row, New York (1981), pp. 530–531.
March, "Advanced Organic Chemistry," John Wiley & Sons, New York (1985), pp. 914–915.
European Search Report No. 95106241.3, Feb. 7, 1995.

*Primary Examiner*—Gary Geist
*Assistant Examiner*—Jean F. Vollano

[57] ABSTRACT

The present invention relates to a process for preparing vinylphosphonic acids of the formula

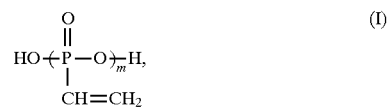

in which m is an integer from 1 to 20 by heating 2-chloroethylphosphonic acids of the formula

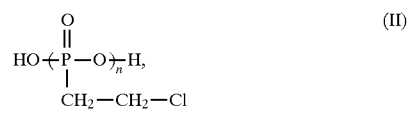

in which n is an integer equal to or smaller than m, if desired in the form of a solution, in the absence or presence of a catalyst to a temperature of 180 to 350° C. and eliminating hydrogen chloride and, where appropriate, water under atmospheric pressure or reduced pressure and, if desired, hydrolysing the vinylphosphonic acids of the formula (I).

19 Claims, No Drawings

PROCESS FOR PREPARING VINYL-PHOSPHONIC ACIDS

This is a continuation of application Ser. No. 08/435,829, filed May 5, 1995, now abandoned.

DESCRIPTION

Process for preparing vinylphosphonic acids

The present invention relates to a process for preparing vinylphosphonic acids of the formula (I)

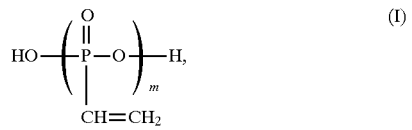

in which m is an integer from 1 to 20. If desired, the vinylphosphonic acid can be converted by a subsequent hydrolysis into vinylphosphonic acid of the formula (I) in which m is 1.

Vinylphosphonic acid, $CH_2=CH-PO(OH)_2$, can be prepared in a known manner by the following method: Phosphorus trichloride is reacted with ethylene oxide, the resulting tris(2-chloroethyl) phosphite is rearranged to give bis(2-chloroethyl) 2-chloroethylphosphonate, followed by reaction of the bis(2-chloroethyl) 2-chloroethylphosphonate with phosgene in the presence of suitable catalysts to give 2-chloroethylphosphonic dichloride (German Patent No. 2,132,962). The 2-chloroethylphosphonic dichloride can then be converted into vinylphosphonic acid by eliminating HCl in the presence of suitable catalysts ($BaCl_2$) and subsequent hydrolysis of the vinylphosphonic dichloride formed (Chem. Abstr. 54, page 265 (1960)).

The process described above for preparing vinylphosphonic acid involves, on the one hand, a comparatively long reaction path of 5 steps and requires a correspondingly high technical expenditure and the use of phosgene as starting material represents a substantial risk. It is known that phosgene can only be handled in an industrial process if extensive, costly safety measures are complied with.

Accordingly, the object was to develop a process for preparing vinylphosphonic acid which does not have the disadvantages described above and moreover can be put into practice in a simple manner even on an industrial scale. In addition to that, the reaction should be started with a starting material which is comparatively readily available and can be obtained in an amount customary in industry.

Surprisingly, this object is achieved by a process for preparing vinylphosphonic acids of the formula (I)

in which m is an integer from 1 to 20, which process comprises heating 2-chloroethylphosphonic acids of the formula (II)

in which n is an integer equal to or smaller than m, if desired in the form of a solution, in the absence or presence of a catalyst to a temperature of 180 to 350° C. and eliminating hydrogen chloride or, where appropriate water under atmospheric pressure or reduced pressure, and, if desired, hydrolysing the vinylphosphonic acids of the formula (I).

The 2-chloroethylphosphonic acids of the formula (II) required for the process according to the invention as starting material are derived from the 2-chloroethylphosphonic acid of the formula (II) in which n is 1 and can be prepared therefrom, if required, by dehydration. As for the 2-chloroethylphosphonic acid, it is used as growth regulator (growth hormone) for plants and accordingly is widely used in agriculture. Consequently 2-chloroethylphosphonic acid is prepared on an industrial scale and is thus a readily available starting material.

The process according to the invention has the advantage of comprising only one reaction step. A further advantage is that the use of hazardous, highly poisonous phosgene is unnecessary.

The 2-chloroethylphosphonic acids of the formula (II) can be used in pure form or else as mixtures of 2-chloroethylphosphonic acids of different degrees of condensation. In connection with this, it may be mentioned that the condensation of 2-chloroethylphosphonic acids provides 2-chloroethylphosphonic acids of the formula (II) where n is greater than 1. If desired, the 2-chloroethylphosphonic acid can also be used in the form of a solution. Examples of suitable solvents are water or lower alcohols, such as aliphatic alcohols having 1 to 5 carbon atoms.

As already mentioned above, the phosphonic acids used are typically 2-chloroethylphosphonic acids of the formula (II) in which n is an integer from 1 to 20. In many cases, 2-chloroethylphosphonic acids of the formula (II) in which n is an integer from 1 to 5 are used. The process according to the invention gives good results if the 2-chloroethylphosphonic acid of the formula (II) used is the 2-chloroethylphosphonic acid of the formula

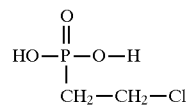

or the 2-chloroethylphosphonic acid in the form of an aqueous solution. Such an aqueous solution containing 2-chloroethylphosphonic acid typically contains 20 to 60, in particular 25 to 50, preferably 30 to 45, % by weight of water.

Another advantage of the process according to the invention is that it can be carried out, as desired or required, in the presence of a catalyst or in the absence of a catalyst. Since, on the one hand, the use of a catalyst can be omitted and, on the other hand, the catalyst can be selected from a comparatively large number of catalysts, the process according to the invention can be carried out in many different ways. It may be particularly surprising that the reaction also gives good results when no catalyst is added.

The catalyst used can be a) compounds containing at least one tri- or pentavalent nitrogen or phosphorus atom which in the case of nitrogen has 1 to 4 valences and in the case of phosphorus at least 3 valences attached to organic radicals having 1 to 20 carbon atoms, where 2 of these valences can form a double bond, b) mono- to tribasic organic or inorganic fully amidated acids of tri- or pentavalent phosphorus whose N-atoms are alkylated by aliphatic radicals having 1 to 20 carbon atoms and whose organic radicals may contain 1 to 20 carbon atoms.

Mixtures of the abovementioned compounds can also be used as the catalyst.

In a large number of cases it is advisable that the catalyst used be a tertiary amine, an acid amide, a quaternary ammonium salt, a tertiary phosphine, a heterocyclic nitrogen compound, a quaternary phosphonium salt, a phosphine oxide or a phosphine imide. If desired, the catalysts used can also be mixtures of the abovementioned substances.

The abovementioned nitrogen and phosphorus compounds which in the case at hand are catalytically active have the formulae

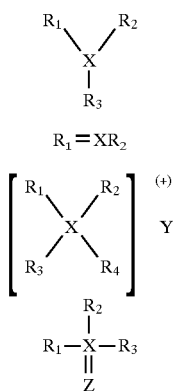

in which the symbols have the following meanings:

X is N or P,

Y is an inorganic or organic acid radical, $R_1$ is an organic radical having 1–20 carbon atoms, each $R_2$ is an organic radical having 1–20 carbon atoms, or is H if X is N, each $R_3$ is an organic radical having 1–20 carbon atoms, or is H if X is N.

In this formula, one of the ligands $R_1$, $R_2$, $R_3$ can, if X is N, be the radical of a mono- or polybasic carboxylic acid or the radical of an inorganic or organic acid of tri- or pentavalent phosphorus or of an amide thereof which may be alkylated.

| | |
|---|---|
| $R_4$ | is an organic radical having 1 to 20 carbon atoms, or is H if X is N, and $R_2$ and $R_3$ are each an organic radical, |
| Z | is O, or S or 2 halogen atoms or $NR_5$ } if X is P, $R_5$ is H or an organic radical having 1 to 20 carbon atoms. |

Thus, X can be an N or P atom, Y can be an inorganic or organic acid radical, for example a halide ion, $SO_4$ ion, a methylsulfate ion or the ion of an organic sulfonic acid.

$R_1$, $R_2$, $R_3$ and $R_4$ can be identical or different organic radicals, for example straight-chain or branched alkyl groups having 1 to 20, preferably 1 to 12, in particular 1 to 4, carbon atoms, alkenyl groups having 2 to 20, preferably 2 to 12, in particular 2 to 4, carbon atoms, cycloalkyl or -alkenyl groups having 4 to 8, preferably 4 to 6, carbon atoms, aryl or aralkyl groups having 6 to 20, preferably 6 to 12, carbon atoms or acyl groups having 1 to 4, preferably 1 to 2, carbon atoms, where all radicals R can in turn again be substituted, preferably monosubstituted, by, preferably, halogen, in particular chlorine and/or bromine or alkoxy radicals having 1 to 4 carbon atoms, preferably 1 to 2 carbon atoms, or a dialkylamino group having alkyl groups of 1 to 4 carbon atoms.

Two of the radicals $R_1$ to $R_4$ can be members of a heterocyclic ring of aromatic or cycloaliphatic nature, which ring may contain further heteroatoms, for example nitrogen, oxygen or sulfur.

In the case where X is nitrogen, $R_2$ and/or $R_3$ and, if $R_2$ and $R_3$ are organic radicals, also $R_4$ can furthermore be hydrogen.

Z can be oxygen or, if X is phosphorus, also sulfur, two hydrogen atoms, preferably 2 chlorine atoms, or the group $NR_5$ where $R_5$ can be H or an organic radical having 1 to 20 carbon atoms.

If X is nitrogen, one of the radicals $R_1$ to $R_3$ can be an acid amide radical or an acid diamide radical of an organic acid of tri- or pentavalent phosphorus whose N atoms can be substituted by alkyl groups having 1 to 18 carbon atoms, preferably 1 to 4 carbon atoms. Preference is given to compounds in which the amide group(s) are monosubstituted, in particular disubstituted, in the manner described. The catalytically active compounds can also contain a plurality of identical or different elements of the meaning X.

The molecular weight of the catalysts used is preferably up to 500, in particular up to 200.

Accordingly, examples of useful catalysts include:

A. Amines, such as trimethylamine, triethylamine, tripropylamine, tributylamine, dimethylethylamine, diethylbutylamine, dimethyldodecylamine, N,N-dimethylaniline, 4-methyl-N,N-dimethylaniline, N,N-diethylaniline, N,N,N',N'-tetramethyl-p-phenylenediamine, triphenylamine, diethylamine, N-butylamine.

B. Heterocyclic nitrogen compounds, such as pyridine, dimethylaminopyridine, quinoline, isoquinoline and alkyl or dialkyl derivatives thereof, preferably methyl or dimethyl derivatives, imidazole, N-vinyl-imidazole, benzimidazole, benzothiazole, benzotriazole, 2-amino-6-ethoxybenzothiazole, 2-hydroxy-5,7-dimethylpyrazolo(1,5,a)pyridimine, N-methyl-pyrrolidine, N-ethylpiperidine, pyrrolidinocyclohexene, triazole, piperidine, and oxides thereof, for example pyridine oxide.

C. Acidamides, for example dimethylformamide, diethylformamide, diethylpropionamide, N,N-dimethylbenzamide, N,N,N',N'-tetramethylterephthalamide, hexamethyl-phosphoric triamide, ethylphosphonic bis(diethyl-amide), methyl-butylphosphinous dimethylamide, diethyl-phosphinous isobutylamide or ureas, such as tetra-methylurea and N,N',N'-trimethyl-N-phenylurea.

D. Quaternary ammonium salts, for example tetramethylammonium chloride or tetramethylammonium bromide, trimethylbenzylammonium chloride, triethylbenzylammonium chloride or triethylbenzylammonium bromide, trimethylchloromethylammonium chloride.

E. Tertiary phosphines, for example trimethylphosphine, triethylphosphine, tripropylphosphine, tributylphosphine, triphenylphosphine, methyldiethylphosphine, dimethylpropylphosphine, diethylbenzylphosphine, tris(p-dimethylaminophenyl) phosphine.

F. Quaternary phosphonium salts, for example tetraethylphosphonium chloride, trimethylbenzylphosphonium chloride, triphenylethylphosphonium 2,4-diaminobenzenesulphonate.

G. Organic compounds of pentavalent phosphorus, for example trimethylphosphine oxide, tributylphosphine oxide, trihexylphosphine oxide, triphenylphosphine oxide, dimethylphenylphosphine oxide, dimethylchloro-methylphosphine oxide, dimethylhexylphosphine oxide, dimethyldodecylphosphine oxide, dimethyleicosyl-phosphine oxide, dimethyl(1-pyrrolidinylmethyl)-phosphine oxide, dimethylphenylphosphine sulfide, dimethyldodecylphosphine sulfide, methyl 2-dimethyl-phosphinyl propionate, 1-methyl-3-phospholene, 1-ethyl-3-methyl-3-phospholene, (2-fluorosulfonyl-ethyl)dimethylphosphine oxide, N-2-dimethyl-phosphinylethyl-N-methylacetamide ,(N-2-dimethyl-phosphinylethyl)methylamine , triphenylphosphine dichloride, dimethylchloromethyldichlorophosphorane, triphenylphosphine imide, triphenylphosphine N-2-hydroxyethylimide.

The catalysts are used in amounts of 0.2 to 5% by weight or more, relative to the 2-chloroethylphosphonic acid used or the polycondensation product used, preferably in amounts of 0.5–2% by weight. They can be used as such or in the form of their salts, preferably of their hydrochlorides.

As already indicated at the beginning, the process according to the invention is carried out at a temperature of 180 to 350° C. and hydrogen chloride and, where appropriate, water are eliminated under atmospheric pressure or reduced pressure.

This reaction can also be carried out in a somewhat modified variation by first eliminating predominantly water at lower temperatures and reduced pressure, for example at 180 to 250° C. and 0.5 to 10 bar, and then eliminating the main portion of the hydrogen chloride at a higher temperature, for example 250 to 280° C. The process can be carried out either under atmospheric pressure or under reduced pressure. If it is intended to use atmospheric pressure, it is advisable to heat the 2-chloroethylphosphonic acids of the formula (II) to 230 to 320° C. and eliminate hydrogen chloride and, where appropriate, water under atmospheric pressure.

In most cases, it is sufficient to heat the 2-chloroethylphosphonic acids of the formula (II) to 200 to 300, in particular to 220 to 285, °C.

If it is intended to use reduced pressure, it is advisable to eliminate hydrogen chloride and, where appropriate, water at a reduced pressure of 0.001 to 500 mbar.

In general, elimination of hydrogen chloride and, where appropriate, water under a reduced pressure of 0.001 to 100 mbar, in particular 0.1 to 20 mbar gives good results.

In order to avoid undesirable side reactions (formation of polymers), it may be advantageous to carry out the process according to the invention in the presence of polymerization inhibitors, for example hydroquinone, hydroquinone monomethyl ether or phenothiazine.

The process can be carried out either batchwise or continuously. Carrying out the process in a continuous mode is particularly favorable. In this mode, the starting material, that is the 2-chloroethylphosphonic acid of the formula (II) is maintained, if desired at a predetermined temperature, in liquid form or is metered into a heated reaction zone which, if desired, is kept under reduced pressure, in the form of the solution, in particular in the case of 2-chloroethylphosphonic acid in the form of an aqueous solution. In the reaction zone, hydrogen chloride and, where appropriate, water are eliminated and condensed in a cooled receiver. When the process is carried out in a suitable manner, an aqueous hydrochloric acid of comparatively high concentration can be recovered.

As a consequence of the elimination of water, more highly condensed vinylphosphonic acids of the formula (I) or more highly condensed 2-chloroethylphosphonic acids of the formula (II) are formed in the course of the reaction. When reaction is complete, a mixture of various vinylphosphonic acids of different degrees of condensation is usually obtained. If desired, the mixture can directly, i.e. in the as-synthesized form, be used further.

However, if it is intended to prepare uncondensed vinylphosphonic acid of the formula (I) in which m is 1, the mixture of the differently condensed vinylphosphonic acids of the formula (I) is hydrolyzed with addition of water.

The examples which follow illustrate the invention without limiting it.

EXPERIMENTAL SECTION

Example 1

106 g (0.733 mol) of liquid 2-chloroethylphosphonic acid heated to 90° C. is added dropwise to a thin-film evaporator heated to 270–275° C. at an initial pressure of 0.5 mbar, as a result of which hydrogen chloride and water escape as gases which are condensed in a cold trap downstream from the apparatus. Over the course of the reaction, the pressure increases to 2 to 3 mbar. After a total of 150 minutes, when the reaction is complete, 69 g of a bottom product containing vinylphosphonic acids is recovered. After reaction is complete, 13.1 g of a 33% hydrochloric acid have accumulated in the cold trap. An aqueous 50% solution is prepared from the vinylphosphonic acids. Based on the $^{31}$P-NMR spectrum, the following components in particular are identified:

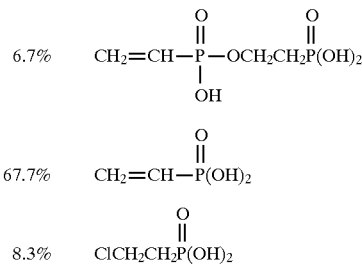

The percentages are based on the total phosphorus content.

The experiment is repeated, using an aqueous 80% solution of 2-chloroethylphosphonic acid which is metered into the thin-film evaporator at room temperature, to give substantially the same result. In this case, 36.5 g of a 33.5% hydrochloric acid accumulates in the cold trap.

Example 2

122 g (0.844 mol) of 2-chloroethylphosphonic acid mixed with 0.6 g of dimethylaminopyridine is heated to 90° C. and added dropwise to a thin-film evaporator heated to 270–275° C. as described in Example 1. 15.4 g of a 33% hydrochloric acid accumulate in a downstream cold trap. 80.7 g of a bottom product containing vinylphosphonic acids is obtained. A 50% aqueous solution is prepared therefrom. Based on the $^{31}$P NMR spectrum, the following components in particular are identified:

5.8%  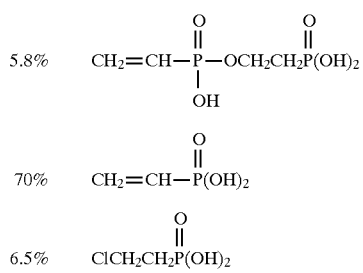

70%  CH₂=CH—P(OH)₂ (with =O)

6.5%  ClCH₂CH₂P(OH)₂ (with =O)

The percentages are based on the total phosphorus content.

Example 3

86.4 g (0.598 mol) of 2-chloroethylphosphonic acid mixed with 0.43 g of triphenylphosphine and 0.26 g of hydroquinone monoethyl ether is heated to 90° C. and added dropwise to a thin-film evaporator heated to 270° C. over a period of 3.5 hours as described in Example 1. 7.3 g of a 33% hydrochloric acid accumulate in a downstream cold trap. 59.7 g of a bottom product containing vinylphosphonic acids is obtained. A 50% aqueous solution is prepared therefrom. Based on the $^{31}$P NMR spectrum, the following components in particular are identified:

7.1%  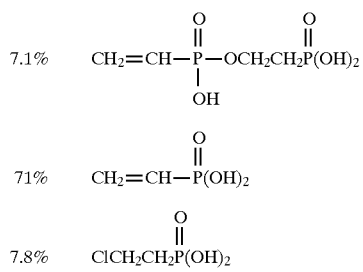

71%  CH₂=CH—P(OH)₂ (with =O)

7.8%  ClCH₂CH₂P(OH)₂ (with =O)

The percentages are based on the total phosphorus content.

Example 4

57.2 g (0.21 mol) of 2-chloroethyldiphosphonic acid is heated to 100° C. and added dropwise to a thin-film evaporator heated to 270° C. as described in Example 1. Only a small amount of hydrochloric acid accumulates in a downstream cold trap. 42.7 g of a bottom product containing vinylphosphoric acids is obtained. An aqueous 50% solution is prepared therefrom. Based on the $^{31}$P NMR spectrum, the following components in particular are identified:

0.6% of polyvinylphosphonic acid 60.8%  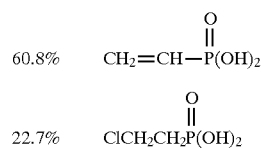

22.7%  ClCH₂CH₂P(OH)₂ (with =O)

The percentages are based on the total phosphorus content.

Example 5

A stirred flask equipped with distillation condenser, distillation receiver, cold trap, vacuum connection is charged with 50 g of vinylphosphonic acid and 1000 g of aqueous 50% chloroethylphosphonic acid. The mixture is heated to 220° C. under vacuum (30 mbar) and then maintained at 220° C. for 4.5 hours. 360 g of a yellowish liquid which, according to its bromine number, contains about 73% of vinylphosphonic acids is obtained as residue. The distillate in the cold trap (610 g) is aqueous 90% hydrochloric acid.

What is claimed is:

1. A process for the preparation of a vinylphosphonic acid of the formula I

in which m is from 1 to 20, comprising:

heating to a temperature in the range of 180 to 350° C. a liquid comprising a compound of the formula II

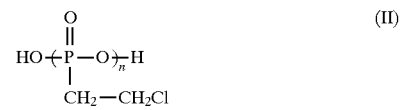

in which n is a number other than zero which is equal to or smaller than m, eliminating hydrogen chloride and, optionally, water, and recovering one or more compounds of the formula I from the thus-reacted liquid as the major product of the process.

2. The process as claimed in claim 1, wherein n is from 1 to 5.

3. The process as claimed in claim 1, wherein said liquid comprising a compound of the formula II is the liquid compound 2-chloroethylphosphonic acid of the formula

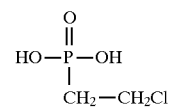

or a compound of formula II in an aqueous solution containing 20 to 60% of water.

4. The process as claimed in claim 1, wherein the compound of the formula (II) is heated to 230 to 320° C., and the eliminating of the hydrogen chloride and, optionally, water is carried out under reduced or atmospheric pressure.

5. The process as claimed in claim 1, wherein the compound of the formula (II) is heated to 200 to 300° C.

6. The process as claimed in claim 1, wherein the compound of the formula (II) is heated to 220 to 285° C.

7. The process as claimed in claim 1, wherein the eliminating of the hydrogen chloride and, optionally, water is carried out under reduced pressure ranging from 0.001 to 500 mbar.

8. The process as claimed in claim 7, wherein said reduced pressure ranges from 0.001 to 100 mbar.

9. The process as claimed in claim 8, wherein said reduced pressure ranges from 0.1 to 20 mbar.

10. The process as claimed in claim 1, wherein the liquid comprising a compound of the formula II is a solution containing said compound.

11. The process as claimed in claim 1, wherein the eliminating of the hydrogen chloride and, optionally, water is carried out in the absence of a catalyst.

12. The process as claimed in claim 1, wherein the eliminating of the hydrogen chloride and, optionally, water is conducted under reduced pressure.

13. The process as claimed in claim 1, wherein, in the compound of formula I which results from the heating of the compound of formula II, water is eliminated from the resulting compound of formula I to form a condensed compound in which m is greater than 1.

14. The process as claimed in claim 13, wherein said condensed compound of formula I is hydrolyzed to produce a compound of formula I having a lower value of m.

15. The process as claimed in claim 13, wherein said heating step is carried out at 200 to 300° C. under atmospheric or reduced pressure.

16. The process as claimed in claim 15, wherein said heating step is carried out under a reduced pressure ranging from 0.001 to 500 mbar.

17. The process as claimed in claim 1, wherein, during the eliminating of the hydrogen chloride and, optionally, water, the temperature or pressure is maintained so as to maintain said compound of formula II in a liquid state or in a liquid solution.

18. The process as claimed in claim 1, wherein the eliminating of the hydrogen chloride and, optionally, water, is carried in the presence of a catalyst comprising at least one compound having at least one tri- or pentavalent or quaternary nitrogen or phosphorus atom or at least one amide of a tri- or pentavalent phosphorus-containing acid or a mixture thereof.

19. A process for the preparation of a vinylphosphonic acid of the formula I

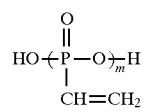

in which m is from 1 to 20, comprising:

heating a liquid comprising a compound of the formula II

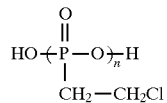

in which n is a number other than zero which is equal to or smaller than m, in the presence of a catalyst, and eliminating hydrogen chloride and, optionally, water, wherein the catalyst is a tertiary amine, an acid amide, a quaternary ammonium salt, a tertiary phosphine, a heterocyclic nitrogen compound, a quaternary phosphonium salt, a phosphine oxide, a phosphine imide or a mixture thereof.

* * * * *